United States Patent
Wakamori et al.

(10) Patent No.: US 9,919,994 B2
(45) Date of Patent: Mar. 20, 2018

(54) ALPHA-HALOTETRAMETHYCYCLO-HEXANONE, A METHOD FOR THE PREPARATION THEREOF, AND A METHOD FOR THE PREPARATION OF A (2,3,4,4-TETRAMETHYLCYCLOPENTYL)METHY CARBOXYLATE COMPOUND

(71) Applicant: SHIN-ETSU CHEMICAL CO., LTD., Tokyo (JP)

(72) Inventors: Shinnosuke Wakamori, Joetsu (JP); Naoki Ishibashi, Joetsu (JP); Miyoshi Yamashita, Joetsu (JP); Takeshi Kinsho, Joetsu (JP)

(73) Assignee: SHIN-ETSU CHEMICAL CO., LTD., Tokyo (JP)

( * ) Notice: Subject to any disclaimer, the term of this patent is extended or adjusted under 35 U.S.C. 154(b) by 0 days.

(21) Appl. No.: 15/581,833

(22) Filed: Apr. 28, 2017

(65) Prior Publication Data

US 2017/0342013 A1 Nov. 30, 2017

(30) Foreign Application Priority Data

May 24, 2016 (JP) .................... 2016-103378

(51) Int. Cl.
| | | |
|---|---|---|
| *C07C 67/00* | (2006.01) | |
| *C07C 67/03* | (2006.01) | |
| *C07C 49/463* | (2006.01) | |
| *C07C 45/62* | (2006.01) | |
| *C07C 45/63* | (2006.01) | |
| *C07C 29/147* | (2006.01) | |

(52) U.S. Cl.
CPC ............ *C07C 67/03* (2013.01); *C07C 29/147* (2013.01); *C07C 45/62* (2013.01); *C07C 45/63* (2013.01); *C07C 49/463* (2013.01); *C07C 67/00* (2013.01); *C07C 2601/08* (2017.05); *C07C 2601/14* (2017.05)

(58) Field of Classification Search
CPC ........ C07C 49/463; C07C 67/14; C07C 45/63; C07C 67/03; C07C 67/00
See application file for complete search history.

(56) References Cited

PUBLICATIONS

Tarantilus et al, Journal of Agricultural and Food Sciences, Isolation and Identification of the Aroma Components from Saffron (*Crocus sativus*), 1997, 45, pp. 459-462.*
J. Millar et al., "Synthesis of the sex pheromone of the obscure mealybug, the first example of a new class of monoterpenoids", www.sciencedirect.com, Tetrahedron Letters 48, pp. 6377-6379, 2007.
Hajare et al., "Enantiospecific synthesis of sex pheromone of the obscure mealybug from pantolactone via tandem conjugate addition/cyclization", Tetrahedron Letters 51, pp. 5291-5293, 2010.
J. Millar et al., "(2,3,4,4-Tetramethylcyclopentyl)Methyl Acetate, A Sex Pheromone From the Obscure Mealybug: First Example of a New Structural Class of Monoterpenes", Journal of Chemical Ecology, vol. 31, No. 12, 2005.

* cited by examiner

*Primary Examiner* — Paul A Zucker
(74) *Attorney, Agent, or Firm* — Oliff PLC

(57) ABSTRACT

A method for the preparation of a sex pheromone of Obscure Mealy bug (OMB), (±)(2,3,4,4-tetramethycyclopentyl) methyl acetate includes a step of subjecting alpha-halotetramethylcyclohexanone to a Favorskii rearrangement to obtain a 2,3,4,4-tetramethylcyclopentane compound (2), a step of subjecting the compound (2) to reduction to obtain (2,3,4,4-tetramethylcyclopentyl)methanol compound (3) and a step of subjection the compound (3) to acylation to obtain a (2,3,4,4-tetramethylcyclopentyl)methyl carboxylate compound (4).

3 Claims, No Drawings

ALPHA-HALOTETRAMETHYCYCLO-HEXANONE, A METHOD FOR THE PREPARATION THEREOF, AND A METHOD FOR THE PREPARATION OF A (2,3,4,4-TETRAMETHYLCYCLOPENTYL)METHY CARBOXYLATE COMPOUND

BACKGROUND OF THE INVENTION

The present invention relates to alpha-halotetramethylcyclohexanone which is useful as a synthetic aroma, and an intermediate in organic chemistry, and a method for the preparation thereof. The present invention relates also to a (2,3,4,4-tetramethylcyclopentyl)methyl carboxylate compound which is useful as a bioactive substance such as a sex pheromone of insects and a substance related therewith. For instance, the invention relates to a method for the preparation of (2,3,4,4-tetramethylcyclopentyl)methyl acetate which is a sex hormone of Pseudococcus viburni, or general name Obscure Mealy bug (hereinafter, called as "OMB").

RELATED ART

Sex pheromones of insects are bioactive substances which have a function that usually, females attracts males. Even a small amount of it shows a high attracting property. Sex pheromones are widely used as a means for predicting breeding or confirming geometric propagation (i.e., invasion into a particular area), and a means for preventing insect pests. Widely practiced means for preventing insects include mass trapping, lure and kill or attract and kill, mating disruption. In the applications of sex pheromones, it is necessary for basic research and applications to economically produce a required amount of a pheromone base.

OMB is prevailing in the American Continents, and damages various crops such as grapes, so that it is a very serious insect pest. Recently, OMB is widening its distribution. Accordingly, it is important to confirm its geometrical spread. J. Millar et al identified a sex pheromone of OMB as (2,3,4,4-tetramethylcyclopentyl)methyl acetate. Further, J. Millar et al conducted attraction experiments with a synthetic racemic substance to show that the synthetic one has an attracting property comparable with the natural pheromone (J. Millar wt al, J. Chem. Ecol., 31. 2999 (2005)).

A method for the selective production of the sex pheromone of OMB is desired for basic biological research and agricultural research of this compound. Strongly desired for application and practical use is an efficient production method which enables a supply of a large amount of the pheromone base An example of the synthesis of the sex pheromone of OMB is described in J. Millar et al, J. Chem. Ecol., 31, 2999 (2005), where synthesis was carried out by use of Nazzarov cyclization reaction, starting with isobutyl methacrylate.

A synthesis method improved over J. Millar et al, J. Chem. Ecol., 31, 2999 (2005) is described in J. Millar et al, Tetrahedron Lett., 48, 6377 (2007). There, use is made of zinc and titanium (IV) chloride instead of the Wittig reaction to improve a yield.

D. Reddy et al reports synthesis of an optically active substance, starting with (−)-pantolactone and using a tandem conjugation addition-cyclization reaction as a key in Tetrahedron Lett., 51, 5291 (2010).

SUMMARY OF THE INVENTION

The method described in J. Millar et al, J. Chem. Ecol., 31, 2999 (2005) is of a short process. However, gas chromatography is used for purifying the desired product, (2,3,4,4-tetramethycyclopentyl)methyl acetate. Accordingly, large scale production of the desired product is very difficult. The method described in J. Millar et al, Tetrahedron Lett., 48, 6377 (2007), uses the Nazarov cyclization with a yield as low as 34%, a conjugation addition at a very low temperature, −78 degrees C., and an oxidation with the use of very poisonous hexa-valent chromium, so that this method is not industrially suitable. In D. Reddy et al, Tetrahedron Lett., 51, 5291 (2010), the synthesis of the desired product, (2,3,4,4-tetramethycyclopentyl)methyl acetate, requires so many as 17 steps and, further, uses a conjugation addition at a very low temperature, −78 degrees C., an oxidation with the use of a highly explosive, high-valent iodine reagent, and a rare metal, Rh. Accordingly, this method is not industrially suitable.

Thus, the previous methods have been thought to be very difficult to produce (2,3,4,4-tetramethycyclopentyl) methyl acetate in an industrial scale due to a yield, separation and purification of intermediate products and the desired product.

The present invention is made under the aforesaid circumstances and provides a method for the production of the sex pheromone of OMB, (2,3,4,4-tetramethycyclopentyl) methyl acetate, taking into consideration attracting activities of optical isomers, in an amount enough for biological research, agricultural research, and applications and practical use. Further, the present invention provides alpha-halotetramethylcyclohexanone useful as an intermediate substance for the synthesis of the pheromones of OMB, and a method for the preparation of alpha-halotetramethylcyclohexanone.

The present inventors have made keen researches and have found that it is possible to efficiently produce a (2,3,4,4-tetramethycyclopentyl) methyl carboxylate compound, starting with alpha-halotetramethylcyclohexanone, and thus completed the present invention.

One embodiment of the present invention provides a method for the preparation of a (2,3,4,4-tetramethylcyclopentyl)methyl carboxylate compound, comprising a step of subjecting alpha-halotetramethylcyclohexanone represented by the following general formula (1a) or (1b):

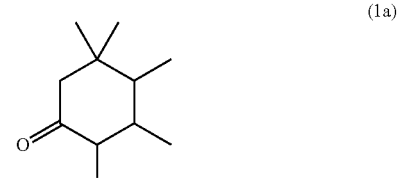

(1a)

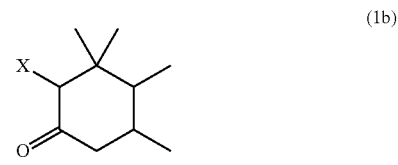

(1b)

wherein X represents a chlorine atom or a bromine atom, to a Favorskii rearrangement to obtain a 2,3,4,4-tetramethylcyclopentane compound represented by the following formula (2):

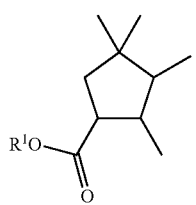

(2)

wherein R¹ represents a hydrogen atom or a monovalent $C_{1-15}$ hydrocarbon group, a step of subjecting the aforesaid 2,3,4,4-tetramethylcyclopentane compound (2) to reduction to obtain (2,3,4,4-tetramethylcyclopentyl)methanol represented by the following formula (3):

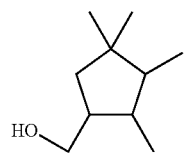

(3)

and a step of subjection the aforesaid (2,3,4,4-tetramethylcyclopentyl)methanol (3) to acylation to obtain a (2,3,4,4-tetramethylcyclopentyl)methyl carboxylate compound represented by the following formula (4):

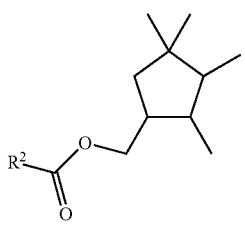

(4)

wherein R² represents a monovalent $C_{1-15}$ hydrocarbon group.

Another embodiment of the invention provides alpha-halotetramethylcyclohexanone represented by the following general formula (1a) or (1b):

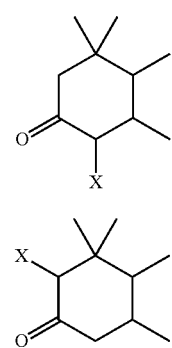

(1a)

(1b)

wherein X represents a chlorine atom or a bromine atom.

Another embodiment of the invention provides a method for the preparation of alpha-halotetramethylcyclohexanone, comprising a step of hydrogenating 3,5,5-trimethyl-4-methylidene-2-cyclohexene-1-one represented by the following formula (5):

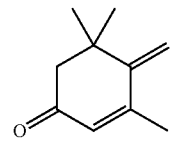

(5)

to obtain 3,3,4,5-tetramethylcyclohexane-1-one represented by the following formula (6):

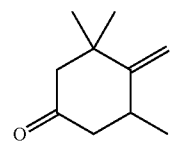

(6)

and a step of subjecting the aforesaid 3,3,4,5-tetramethylcyclohexane-1-one (6) to halogenation to obtain alpha-halotetramethylcyclohexanone represented by the following general formula (1a) or (1b):

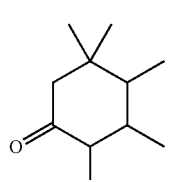

(1a)

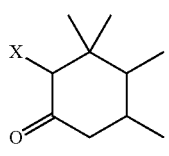

(1b)

wherein X represents a chlorine atom or a bromine atom.

According to the invention, 3,3,4,5-tetramethylcyclohexane-1-one (6) and the alpha-halotetramethylcyclohexanone (1a) or (1b) which is useful as an intermediate substance are efficiently prepared starting with 3,5,5-trimethyl-4-methylidene-2-cyclohexene-1-one (5). Further, the 2,3,4,4-tetramethylcyclopentane compound (2), (2,3,4,4-tetramethylcyclopentyl)methanol (3) and the (2,3,4,4-tetramethylcyclopentyl)methyl carboxylate compound are efficiently prepared using the aforesaid alpha-halotetramethylcyclohexanone (1a) or (1b) in mild conditions, without using a toxic agent or a highly explosive agent.

DETAILED DESCRIPTION OF THE PREFERRED EMBODIMENTS

The intermediate substances, the agents and the desired products may comprise stereo-isomers such as those with different substitution positions, enantiomers and diastereomers. Unless otherwise mentioned, the indications on these compounds, for instance by chemical formulas, in the present specification include all of the isomers. The isomers may be used as a single isomer or a mixture of isomers.

The present inventors have chosen the 2,3,4,4-tetramethylcyclopentane compound (2) as an intermediate substance in the preparation of the (2,3,4,4-tetramethylcyclopentyl) methyl carboxylate compound (4), such as (2,3,4,4-tetramethylcyclopentyl)methyl acetate which is a sex pheromone of OMB. The 2,3,4,4-tetramethylcyclopentane compound (2) may be converted to (2,3,4,4-tetramethylcyclopentyl) methanol (3) by reduction, which may further be acylated to give the (2,3,4,4-tetramethylcyclopentyl)methyl carboxylate compound (4). The intermediate substance, 2,3,4,4-tetramethylcyclopentane compound (2), is one of the products obtained by subjecting alpha-halotetramethylcyclohexanone (1a) or (1b) to action of an base. For instance, when alpha-halotetramethylcyclohexanone (1a) is subjected to the action of a base, it may be thought that two different hydrogen atoms, $H_a$ and $H_b$, react (see the following scheme). When $H_a$ reacts, a Favorskii rearrangement occurs. When $H_b$ reacts, beta-elimination occurs. Thus, the two products may be formed. The product enclosed by solid lines in the following scheme is one produced through the reaction of $H_a$; and the product enclosed by dotted lines is one produced through the reaction of $H_b$. In the scheme, $R^1$ is a hydrogen atom or a monovalent $C_{1-15}$ hydrocarbon group.

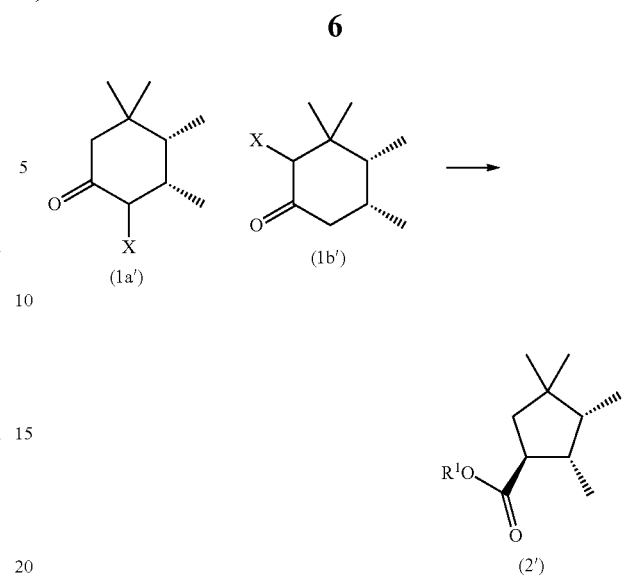

Hereinafter, embodiments of the present invention will be explained in detail, but the invention shall not be limited thereby.

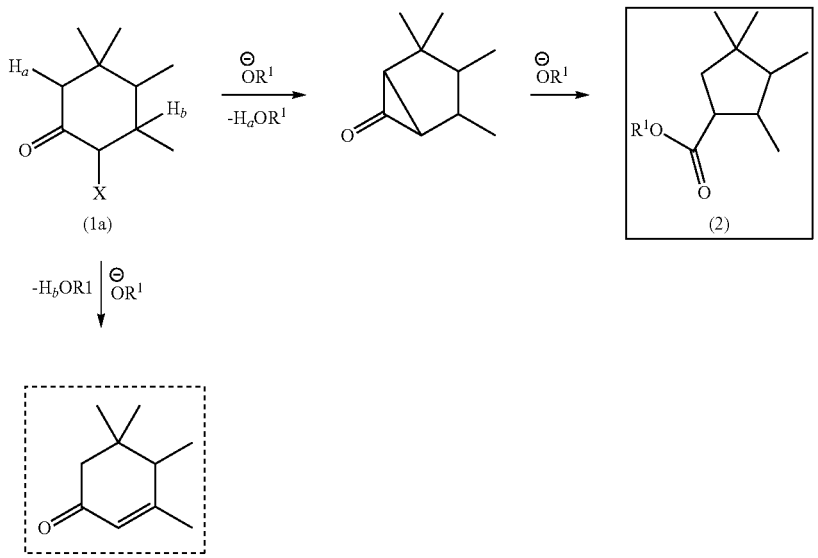

The present inventors were interested in a resulting ratio between the these products obtained by the action of a base on alpha-halotetramethylcyclohexanone (1a) or (1b) in various conditions and have found that the Vavorskii rearrangement, i.e., reaction of Ha, occurs predominantly in the presence of various bases (nucleophilic reagents) to give the 2,3,4,4-tetramethylcyclopentane compound (2) in a high yield.

The present inventors have also found that when a starting substance is alpha-halotetramethylcyclohexanone with the methyl groups at positions 3 and 4 being in a cis-conformation, as indicated in the following formulas (1a') or (1b'), 2,3,4,4-tetramethylcyclopentane compound (2') is obtained in a high selectivity, which has the same relative stereo-configuration as that of (2,3,4,4-tetramethylcyclopentyl) methyl acetate which is a sex pheromone of OMB.

3,5,5-Trimethyl-4-methylidene-2-cyclohexene-1-one which may be a starting substance to synthesize alpha-halotetramethylcyclohexanone (1a) or (1b) is represented by the following formula (5).

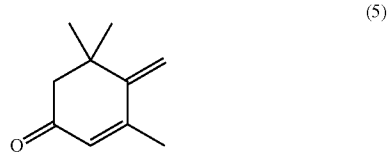

A method to prepare 3,5,5-trimethyl-4-methylidene-2-cyclohexene-1-one (5) may include acid treatment of 1,4-dioxaspiro[4.5]-8-methylidene-7,9,9-trimethyl-6-decene.

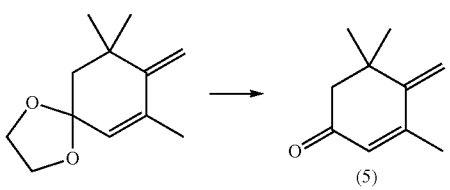

(5)

Next, synthesis of 3,3,4,5-tetramethylcyclohexane-1-one (6) by hydrogenation of 3,5,5-trimethyl-4-methylidene-2-cyclohexene-1-one (5) will be explained.

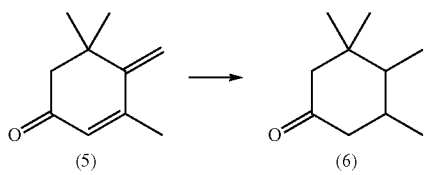

(5)　　(6)

Catalyst to be used in the hydrogenation of compound (5) includes metals such as cobalt, nickel, rhodium, palladium, ruthenium, osmium, platinum, iridium, copper and iron, and oxides, hydroxides and halogenide thereof. These may be used alone or in combination. The aforementioned metal catalyst may be supported on a carrier, such as carbon, alumina, zeolite, and silica gel. A particularly preferred catalyst is palladium carbon.

A solvent to be used in the hydrogenation of compound (5) includes alcohols such as methanol, ethanol, isopropyl alcohol, t-butyl alcohol, benzyl alcohol, methoxyethanol, ethoxyethanol, diethyleneglycol monomethylether, and triethyleneglycol monomethylether; ethers such as diethyether, di-n-butylether, tetrahydrofurane and 1,4-dioxane; hydrocarbons such as hexane, heptane, benzene, toluene, xylene and cumene; aprotic polar solvents such as N,N-dimethylformamide (DMF), 1,3-dimethyl-2-imidazolidinone (DMI), dimethylsulfoxide (DMSO), and hexamethylphosphoric triamide (HMPA); and nitriles such as acetonitrile, and propionitrile. These may be used alone or in combination.

An amount of the solvent in the hydrogenation is 0.01 to 100,000 parts, preferably 0.1 to 10,000 parts, more preferably 1 to 1,000 parts, relative to 100 parts of the substrate, compound (5).

A pressure in the hydrogenation of compound (5) is preferably from normal pressure to 5 MPa, and a reaction temperature is preferably 5 to 70 degrees C., more preferably 20 to 50 degrees C.

A reaction time in the hydrogenation is not limited. It is preferred in view of yield that the reaction is completed, as followed by gas chromatography (GC) or thin layer chromatography (TLC). Then, the reaction time is preferably 5 minutes to 240 hours.

After-treatment of the reaction, isolation and purification of the desired product may be carried out in a conventional manner properly chosen from ones usually used in organic syntheses, such as reduced-pressure distillation and various chromatographies. When a crude product has a satisfactory purity, the crude product may be used as such in the next step.

When (plus/minus) (2,3,4,4-tetramethylcyclopentyl) methyl acetate, sex pheromone of OMB, is desired, it is preferred that the methyl groups at positions 4 and 5 in compound (6) have a cis-configuration as indicated in the following formula (6'). A hydrogen atom forms bonding on a sterically open side of the molecule in the hydrogenation. Accordingly, compound (6') is formed in a high selectivity from compound (5). The relative configuration of the methyl groups in compound (6') obtained is maintained in the subsequent reactions.

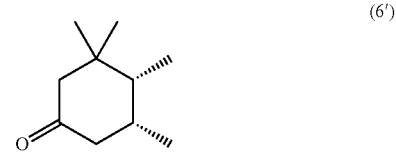

(6')

Next, the synthesis of alpha-halotetramethylcyclohexanone (1a) or (1b) by halogenation of 3,3,4,5-tetramethylcyclohexane-1-one (6) will be explained.

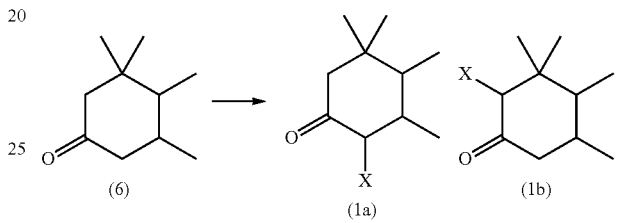

(6)　　(1a)　　(1b)

X in the formulas is a chlorine atom or a bromine atom. A chlorine atom or a bromine atom is selected in view of boiling points of compounds in a case where purification is needed, or in view of adjusting polarities. A bromine atom is particularly preferred on account of availability of raw materials.

Alpha-halotetramethylcyclohexane comprises regioisomers and diastereomers of compound (1a) or (1b). Use of either of R-(1a), S-(1a), R-(1b), S-(1b) as indicated below leads to formation of one and the same desired product, 2,3,4,4-tetramethylcyclopentane compound. Therefore, position selectivity or stereo-selectivity needs not be considered. Thus, either one of R-(1a), S-(1a), R-(1b), S-(1b) or a mixture thereof in any ratio may be used.

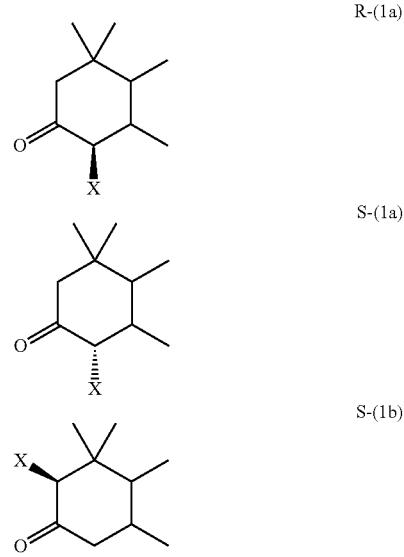

R-(1a)

S-(1a)

S-(1b)

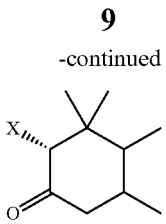

R-(1b)

A reagents to be used for the halogenation of compound (6) includes, for instance, halogen molecules such as bromine and chlorine molecules, halogenated amides such as N-bromosuccinimide (NBS), N-chlorosuccinimide (NCS), 1,3-dibromo-5,5-dimethyl hydantoin, and perbromo pyridine bromide; halogenation reagents having a carbon-halogen bond, such as 5,5-dibromo Meldrum' acid, 2,4,4,6-tetrabromo-2,5-cyclohexadienone. These may be used alone or in combination. Halogen molecules are preferred on account of reaction conditions, easy after-treatment and easy separation of products.

An amount of the halogenation reagent depends upon kinds of the substrate, i.e., compound (6), and the bases, and is in general 0.0001 mole to 10,000 moles, preferably 0.001 mole to 1,000 moles, further preferably 0.001 mole to 100 moles, per mole of the substrate.

A solvent to be used in the halogenation includes water; carboxylic acid solvents such as formic acid and acetic acid; alcohols such as methanol and ethanol; ethers such as diethyl ether, di-n-butyl ether, tetrahydrofurane and 1,4-dioxane; and hydrocarbons such as hexane and heptane. These may be used alone or in combination.

An amount of the solvent in the halogenation is 0.01 to 100,000 parts, preferably 0.1 to 10,000 parts, more preferably 1 to 1,000 parts, relative to 100 parts of the substrate, compound (6). A reaction time in the halogenation is not limited. It is preferred in view of a yield that the reaction is completed, as followed by gas chromatography (GC) or thin layer chromatography (TLC). Then, the reaction time is preferably 5 minutes to 240 hours.

After-treatment of the reaction, isolation and purification of the desired product may be carried out in any conventional manner properly chosen from ones usually used in organic syntheses, such as reduced-pressure distillation and various chromatographyies. When a crude product has a satisfactory purity, the crude product may be used as such in the next step.

Next, will be explained the synthesis of the 2,3,4,4-tetramethylcyclopentane compound (2) by a Favorskii rearrangement of alpha-halotetramethylcyclohexanone (1a) or (1b).

The Favorskii rearrangement may be carried out in various conditions, and is basically a process where the compound (1a) or (1b) which has a halogen atom is converted into a cyclopropane intermediate (1x) (see the following scheme), which is then subjected to a reaction with a nucleophilic reagent.

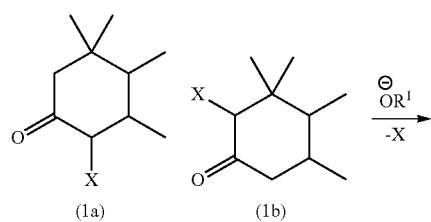

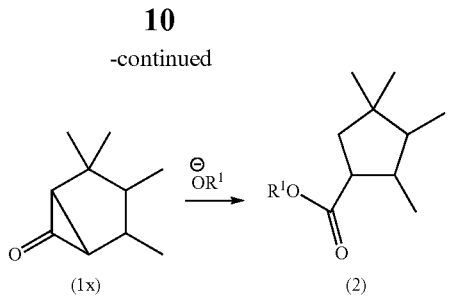

wherein $R^1$ is as defined above.

The intermediate (1x) is thought to be unstable.

The Favorskii rearrangement of compound (1a) or (1b) may be a nucleophilic reaction in the presence of a base.

Preferred examples of the base include alkoxides such as sodium methoxide, sodium ethoxide, sodium t-butoxide, sodium t-amiloxide, lithium methoxide, lithium ethoxide, lithium t-butoxide, lithium t-amiloxide, potassium methoxide, potassium ethoxide, potassium t-butoxide and potassium t-amiloxide; and hydroxide salts such as sodium hydroxide, lithium hydroxide, potassium hydroxide and barium hydroxide. These bases may be used alone or in combination, and may be selected, taking kinds of the substrate, reactivity and selectivity into consideration.

An amount of the base depends on kinds of the substrates and the bases, and is in general 0.0001 to 10,000 moles, preferably 0.001 to 1,000 moles, more preferably 0.001 to 100 moles, per mole of the substrate, compound (1a) or (1b).

In a case where an alkoxide is chosen as the base, preferred is an alkoxide comprising an alkoxide moiety, $R^1O^-$, which corresponds to the substituent, $CO_2R^1$, in the compound (2). Then, it can be avoided that the reaction system is complicated due to transesterification. Further, this base is preferred also as a reagent for the second step, i.e., the conversion of intermediate (1x) into compound (2).

The Favorskii rearrangement of compound (1a) or (1b) may be carried out in the presence or absence of a solvent, at room temperature or with cooling or warming as needed.

The solvent to be used in the Favorskii rearrangement includes water; liquid ammonium; alcohols such as methanol and ethanol; ethers such as diethyl ether, di-n-butyl ether, tetrahydrofurane and 1,4-dioxan; hydrocarbons such as hexane, heptane, benzene, toluene, xylene and cumene; ketones such as acetone and 2-butanone; esters such as ethyl formate, methyl acetate, ethyl acetate, butyl acetate and n-amyl acetate; aprotic polar solvents such as N,N-dimethyl formamide, 1,3-dimethyl-2-imidazolidinone, dimethyl sulfoxide and hexamethyl phosphoric triamide; nitriles such as acetonitrile and propionitrile; and amines such as pyridine, ethylamine, diethylamine, triethylamine, aniline, and dimethylaniline. These may be used alone or in combination.

An amount of the solvent to be used in the Favorskii rearrangement is 0.01 to 100,000 parts, preferably 0.1 to 10,000 parts, more preferably 1 to 1,000 parts, relative to 100 parts of the substrate. In a case where an alcohol is chosen as the solvent, preferred is an alcohol, $R^1OH$, which corresponds to the substituent, $CO_2R^1$, in the compound (2). Then, it can be avoided that the reaction system is complicated due to transesterification.

A reaction temperature and a reaction time in the Favorskii rearrangement of compound (1a) or (1b) are not limited. It is preferred to proceed sufficiently with the reaction, as followed by gas chromatography (GC) or thin layer chromatography (TLC). The reaction temperature is preferably 0 degree C. to a boiling point of a solvent, more preferably 10 to 100 degrees C. The reaction time is usually 5 minutes to 240 hours.

It has been found that in the production of 2,3,4,4-tetramethylcyclopenane compound (2) through the Favorskii rearrangement of alpha-halotetramethylcyclohexanone (1a) or (1b), compound (2) is obtained in an industrially satisfactory yield and selectivity by choosing proper reaction conditions among the aforesaid various conditions. It is noted that a beta-elimination product, 3,4,5,5-tetramethylcyclohexa-2-en, which is thought to be relatively stable, is scarcely formed. In addition, al of the regional isomers and stereo-isomers of alpha-halotetramethylcyclohexanone, i.e., R-(1a), S-(1a), R-(1b) and S(1b), give the same envisaged product, that is, the reaction is regiochemically and stereochemically convergent, but not regiospecific nor stereospecific, so that discriminative production among the regional isomers and the stereo-isomers is unnecessary, which is industrially valuable. It is though that such a high selectivity is on account of $H_b$ in compound (1a) being in a narrow space.

When use is made of 3,3,4,5-tetramethylcyclohexane-1-one (6') with the methyl groups at positions 4 and 5 being in cis-configuration, 2,3,4,4-tetramethylcyclopentane compound (2'), which has the same relative stereo-configuration as that of (2,3,4,4-tetramethylcyclopentyl)methyl acetate, sex pheromone of OMB, is obtained through (1a') or (1b') in a high yield.

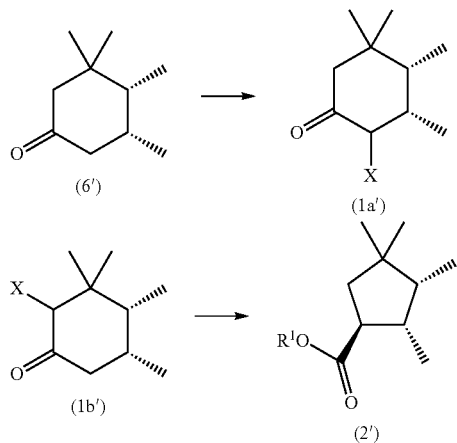

When the envisaged 2,3,4,4-tetramethylcyclopenane compound (2) produced by the Favorskii rearrangement has a satisfactory purity, the crude product may be used as such in the next step, or may be purified by any purification means conventional in organic synthesis chemistry such as distillation, various chromatographies and crystallization.

Next, the synthesis of (2,3,4,4-tetramethylcyclopentyl)methanol (3) by reduction of the 2,3,4,4-tetramethylcyclopentane compound (2) thus obtained will be explained.

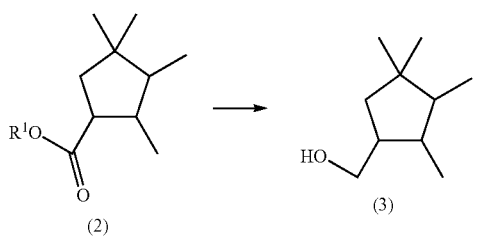

The 2,3,4,4-tetramethylcyclopentane compound (2) may be directly converted into (2,3,4,4-tetramethylcyclopentyl)methanol (3) by the reduction as will be explained below. Alternatively, when $R^1$ is a monovalent $C_{1-15}$ hydrocarbon group, the 2,3,4,4-tetramethylcyclopentane compound (2) is converted into 2,3,4,4-tetramethylcyclopentanoic acid, which is then reduced. The conversion of the 2,3,4,4-tetramethylcyclopentane compound (2) into 2,3,4,4-tetramethylcyclopentanoic acid will first be explained below.

In a case where $R^1$ is a monovalent $C_{1-15}$ hydrocarbon group, a conventional conversion reaction of an ester into a carboxylic acid may be used for the conversion of the 2,3,4,4-tetramethylcyclopentane compound (2) into 2,3,4,4-tetramethylcyclopentanoic acid. For instance, a hydrolysis in a basic or neutral condition and an elimination reaction in an acidic condition may be used. The hydrolysis is preferred when $R^1$ in the substrate ester is a primary or secondary hydrocarbon group. The elimination reaction in an acidic condition is preferred when $R^1$ is a tertiary hydrocarbon group. The hydrolysis is carried out usually in a solvent with the use of a base or a salt, followed by addition of water in a solvent, or water. The elimination reaction is carried out usually in a solvent with the use of an acid. Cooling or warming may be used in either reaction, if needed.

Example of the base to be used in the hydrolysis include hydroxides such as metal hydroxides, preferably hydroxides of alkali metals or alkali earth metals, such as sodium hydroxide, lithium hydroxide, potassium hydroxide, and barium hydroxide; carbonate salts such as carbonates or hydrogen carbonates of alkali metals, such as sodium carbonate, potassium carbonate, sodium hydrogen carbonate, and potassium hydrogen carbonate; and alkoxides, preferably metal alkoxides, more preferably alkali metal alkoxides such as sodium methoxide, sodium ethoxide, sodium t-butoxide, sodium t-amyloxide, lithium methoxide, lithium ethoxide, lithium t-butoxide, lithium t-amyloxide, potassium methoxide, potassium ethoxide, potassium t-butoxide, and potassium t-amyloxide.

Examples of the salt to be used in the hydrolysis include halides such as alkali metal halides such as lithium iodide, lithium bromide, trimethylsilyl iodide, and trimethylsilyl bromide.

Examples of the acid to be used in the elimination reaction include inorganic acids such as hydrochloric acid, hydrobromic acid, hydroiodic acid, sulfuric acid, nitric acid, boric acid and phosphoric acid, and salts thereof, such as potassium hydrogen sulfate; organic acids such as formic acid, acetic acid, propionic acid, oxalic acid, trifluoroacetic acid, methanesulfonic acid, benzenesulfonic acid, p-toluenesulfonic acid and naphthalenesulfonic acid, and salts thereof; Lewis acids such as aluminum trichloride, aluminum ethoxide, aluminum isopropoxide, aluminum oxide, boron trifluoride, boron trichloride, boron tribromide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide; oxides such as alumina, silica gel and titania. These may be used alone or in combination.

Examples of the solvent to be used in the hydrolysis or the elimination reaction include water; alcohols such as methanol, ethanol, isopropyl alcohol, t-butyl alcohol, benzyl alcohol, methoxyethanol, ethoxyethanol, diethyleneglycol monomethylether, and triethyleneglycol monomethylether; ethers such as diethyether, di-n-butylether, tetrahydrofurane and 1,4-dioxane; hydrocarbons such as hexane, heptane, benzene, toluene, xylene and cumene; aprotic polar solvents such as N,N-dimethylformamide (DMF), 1,3-dimethyl-2-imidazolidinone (DMI), dimethylsulfoxide (DMSO), and hexamethylphosphoric triamide (HMPA); and nitriles such as acetonitrile, and propionitrile. These may be used alone or in combination.

An amount of the solvent in the hydrolysis or the elimination reaction is 0.01 to 100,000 parts, preferably 0.1 to 10,000 parts, more preferably 1 to 1,000 parts, relative to 100 parts of the substrate, compound (2).

A reaction temperature and a reaction time in the hydrolysis or the elimination reaction are not limited. It is preferred to proceed sufficiently with the reaction, as followed by gas chromatography (GC) or thin layer chromatography (TLC). The reaction temperature is preferably −78 degree C. to a boiling point of the solvent, more preferably −10 to 100 degrees C. The reaction time is usually 5 minutes to 240 hours.

After-treatment of the reaction, isolation and purification of the desired product may be carried out in any conventional manner properly chosen from ones usually used in organic syntheses, such as reduced-pressure distillation and various chromatographyies. When a crude product has a satisfactory purity, the crude product may be used as such in the next step.

Next, explained will be the case where the 2,3,4,4-tetramethylcyclopentane compound (2) is directly reduced and the case where the 2,3,4,4-tetramethylcyclopentane compound (2) is converted into 2,3,4,4-tetramethylcyclopentanoic acid, which is then reduced into (2,3,4,4-tetramethylcyclopentyl)methanol (3).

Any known reduction manners from a carboxylate ester or carboxylic acid into an alcohol may be applied for the aforesaid reduction. In the reduction, a reaction substrate is reacted with a reducing agent usually in a solvent and, if needed, with cooling or warming. A choice of a proper reaction substrate depends on a reducing agent to be used and reaction conditions. When $R^1$ in the ester is a primary or secondary alkyl group, the 2,3,4,4-tetramethylcyclopentane compound (2) itself may preferably be the substrate. In a case where $R^1$ is tertiary, in particular sterically much hindered, a rate of the reduction may be slow. In such a case, the 2,3,4,4-tetramethylcyclopentane compound (2) is preferably converted into 2,3,4,4-tetramethylcyclopentanoic acid, which is then a substrate for the reduction.

Examples of the reducing agent to be used in the reduction include hydrogen; boron compounds such as borane, alkyl borane, dialkyl borane and bis(3-methyl-2-butyl) borane; metal hydrides such as dialkylsilane, trialkylsilane, monoalkylaluminium hydride and dialkylaluminium hydride; and complex hydrides such as sodium borohydride, lithium borohydride, potassium borohydride, calcium borohydride, sodium aluminium hydride, lithium aluminium hydride, sodium trimethoxy borohydride, lithium trimethoxy aluminium hydride, lithium diethoxy aluminium hydride, lithium tri-t-butoxy aluminium hydride, sodium bis(2-methoxyethoxy) aluminium hydride, lithium triethylborohidride and aluminium diisobutyl halide, and their alkoxy or alkyl derivatives. Complex hydrides are preferred on account of reaction conditions, easy after-treatment and easy isolation of products.

An amount of the reducing agent in the reduction depends on a reducing agent to be used and reaction conditions, but is preferably, in general, 0.5 mole to large excess (such as 2 to 500 moles), more preferably 0.9 to 8.0 moles, per mole of the substrate.

The solvent to be used in the reduction includes water; hydrocarbons such as hexane, heptane, benzene, toluene, xylene and cumene; ethers such as diethyl ether, di-n-butyl ether, diethyleneglycol diethyl ether, diethyleneglycol dimethyl ether, tetrahydrofurane and 1,4-dioxan; alcohols such as methanol, ethanol, 1-propanol, 2-propanol, ethyleneglycol monomethyl ether, and diethyleneglycol monomethyl ether; nitriles such as acetonitrile; ketones such as acetone and 2-butanone; esters such as ethyl acetate and n-butyl acetate; and aprotic polar solvents such as N,N-dimethyl formamide, dimethyl sulfoxide and hexamethyl phosphoric triamide. These may be used alone or in combination.

A solvent in the reduction is properly chosen, depending upon a reducing agent to be use. For instance, a preferred combination of the solvent with the reducing agent is an ether or a mixed solvent comprising an ether and an alcohol in combination with lithium borohydride as the reducing agent; or an ether or a mixed solvent comprising an ether and hydrocarbon in combination with lithium aluminum hydride as the reducing agent.

An amount of the solvent in the reduction is 0.01 to 100,000 parts, preferably 0.1 to 10,000 parts, more preferably 1 to 1,000 parts, relative to 100 parts of the substrate (2).

A reaction temperature and a reaction time in the reduction may vary, depending upon an agent and solvent to be used. For instance, when lithium aluminium hydride in tetrahydrofurane is used as the reducing agent, a reaction temperature is preferably −78 to 50 degrees C., more preferably −70 to 20 degrees C. The reaction time is not limited. It is preferred in view of a yield to proceed sufficiently with the reaction, as followed by gas chromatography (GC) or thin layer chromatography (TLC). The reaction time is, usually, approximately 0.5 to 96 hours.

When a starting material in the reduction is 2,3,4,4-tetramethylcyclopentane compound represented by the following formula (2'), which has the same relative stereoconfiguration as that of (2,3,4,4-tetramethylcyclopentyl) methyl acetate, sex pheromone of OMB, (2,3,4,4-tetramethylcyclopentyl)methanol represented by the following formula (3') is obtained.

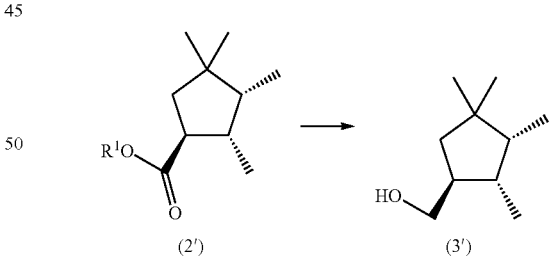

Isolation and purification of (2,3,4,4-tetramethylcyclopentyl)methanol (3) thus obtained may be carried out in any conventional manner properly chosen from ones usually used in organic syntheses, such as reduced-pressure distillation and various chromatographyies. Reduced-pressure distillation is preferred in view of industrial economy. When a crude product (3) has a satisfactory purity, the crude product may be used as such in the next step.

Next, explained will be the synthesis of (2,3,4,4-tetramethylcyclopentyl) methyl carboxylate (4) by esterification of (2,3,4,4-tetramethylcyclopentyl)methanol (3).

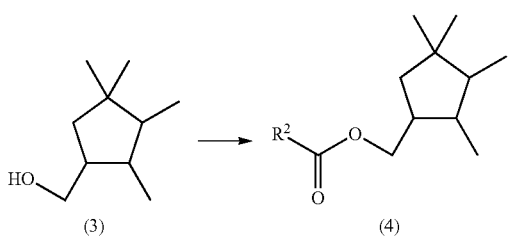

wherein R² represents a monovalent $C_{1-15}$ hydrocarbons.

R² may be as mentioned above for R², and is preferably a methyl, ethyl, n-propyl, isopropyl, isobutyl, sec-butyl, 4-methyl pentyl, 2-methyl-1-propenyl or 2-methyl-2-propenyl group.

For the preparation of (2,3,4,4-tetramethylcyclopentyl) methyl carboxylate (4) by esterification of (2,3,4,4-tetramethylcyclopentyl)methanol (3), use is made of any known method for the preparation of esters, such as a reaction with an acylating agent, a reaction with a carboxylic acid, a transesterification, and conversion of compound (3) into an alkylating agent which is then reacted with a carboxylic acid.

For the reaction with an acylating agent, the substrate, (2,3,4,4-tetramethylcyclopentyl)methanol (3), is brought into contact with, simultaneously or sequentially, an acylating agent and a base or acid catalyst in a single solvent or a solvent mixture.

The solvent to be used in the acylation includes chlorinated solvents such as methylene chloride, chloroform and trichloroethylene; hydrocarbons such as hexane, heptane, benzene, toluene, xylene and cumene; ethers such as diethyl ether, di-n-butyl ether, diethyleneglycol diethyl ether, diethyleneglycol dimethyl ether, tetrahydrofurane and 1,4-dioxan; nitriles such as acetonitrile; ketones such as acetone and 2-butanone; esters such as ethyl acetate and n-butyl acetate; and aprotic polar solvents such as N,N-dimethyl formamide, dimethyl sulfoxide and hexamethyl phosphoric triamide. These may be used alone or in combination.

Examples of the acylating agent include carboxylic acid chloride, carboxylic acid bromide, carboxylic acid anhydride, carboxylic acid-trifluoroacetic acid mixture anhydride, carboxylic acid-methanesulfonic acid mixture anhydride, carboxylic acid benzenesulfonic acid mixture anhydride, carboxylic acid-p-toluenesulfonic acid mixture anhydride, and carboxylic acid-p-nitrophenyl.

Examples of the base preferably include triethylene amine, diisopropylethylamine, N,N-dimethylaniline, pyridine, and 4-dimethylaminopyridine.

In the reaction with an acylating agent such as an acid anhydride, the reaction may be conducted in the presence of acid catalyst instead of the base. Example of the acid catalyst include inorganic acids such as hydrochloric acid, hydrobromic acid, sulfuric acid and nitric acid; organic acids such as oxalic acid, trifluoroacetic acid, methanesulfonic acid, benzenesulfonic acid and p-toluenesulfonic acid; and Lewis acids such as aluminum trichloride, aluminum ethoxide, aluminum isoporopoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide.

A proper reaction temperature may chosen, depending upon an acylating agent to be used and reaction conditions and, in general, preferably −50 degrees C. to a boiling points of a solvent, more preferably −20 degrees C. to room temperature (i.e., 5 to 35 degrees. C, hereinafter the same). An amount of the acylating agent is 0.8 to 500 moles, preferably 0.8 to 50 moles, further preferably 0.8 to 5 moles, per mole of the starting material, compound (3).

The reaction with a carboxylic acid is a dehydration reaction of (2,3,4,4-tetramethylcyclopentyl)methanol (3) with a carboxylic acid, generally, in the presence of an acid catalyst. An amount of the carboxylic acid is 0.8 to 500 moles, preferably 0.8 to 50 moles, further preferably 0.8 to 5 moles, per mole of the starting material, compound (3).

Example of the acid catalyst to be used in the reaction of compound (3) with a carboxylic acid include inorganic acids such as hydrochloric acid, hydrobromic acid, sulfuric acid and nitric acid; organic acids such as oxalic acid, trifluoroacetic acid, methanesulfonic acid, benzenesulfonic acid and p-toluenesulfonic acid; and Lewis acids such as aluminum trichloride, aluminum ethoxide, aluminum isoporopoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium (IV) ethoxide, titanium(IV) isopropoxide and titanium(IV) oxide. These may be used alone or in combination. An amount of the acid catalyst is 0.0001 to 100 moles, preferably 0.001 to 1 mole, more preferably 0.01 to 0.05 mole, per mole of the starting material, compound (3).

The solvent to be used in the reaction of compound (3) with a carboxylic acid may be the solvents mentioned for the reaction with the acylating agent.

A temperature in the reaction of compound (3) with a carboxylic acid may be properly chosen, depending upon carboxylic acid to be used and reaction conditions and is, in general, preferably −50 degrees C. to a boiling point of a solvent, more preferably room temperature to a boiling point of a solvent. The reaction may be carried out, while removing formed water via azeotropic distillation with a hydrocarbon such as hexane, heptanes, benzene, toluene, xylene and cumene. In such a case, water may be distilled off under reflux at a boiling point of the solvent at normal pressure, or at a temperature lower than the boiling point, in a reduced pressure.

An alternative method may be used for the reaction with a carboxylic acid, wherein carboxylic acid is reacted with a condensing agent, which is then condensation-reacted with (2,3,4,4-tetramethylcyclopentyl)methanol (3) in basic conditions. An amount of the carboxylic acid is 0.8 to 500 moles, preferably 0.8 to 50 moles, further preferably 0.8 to 5 moles, per mole of the starting material, compound (3).

Examples of the condensing agent include carbodiimides such as N,N'-dicyclohexyl carbodiimide (DCC), and 1-ethyl-3-(3-dimethylaminopropyl) carbodiimide (EDC); and uroniums such as O-(7-aza-1H-benzotriazol-1-yl)-N,N,N',N'-tetramethyluronium hexafluorophosphate (HATU) and O-(benzotriazol-1-yl)-N,N,N',N'-tetramethyluronium hexafluorophosphate (HBTU). These may be used alone or in combination. An amount of the condensing agent is 0.8 to 500 moles, preferably 0.8 to 50 moles, further preferably 0.8 to 5 moles, per mole of the starting material, compound (3).

Examples of the base include triethylamine, diisopropylethylamine, N,N-dimethylaniline, pyridine, and 4-dimethylaminopyridine.

A solvent to be used in the condensation reaction of compound (3) with a carboxylic acid, using a condensing agent, may be the solvents mentioned for the reaction with the acylating agent.

A reaction temperature in the condensation reaction of compound (3) with a carboxylic acid, using a condensing agent, may properly be chosen, depending upon a carboxylic acid to be used and reaction conditions and is, in general, −50 degrees C. to a boiling point of the solvent, more preferably room temperature to a boiling point of the solvent.

The transesterification is carried out by reacting (2,3,4,4-tetramethylcyclopentyl)methanol (3) with an alkyl carboxylate in the presence of an acid catalyst, while removing a formed alkyl alcohol. Examples of the alkyl carboxylate are preferably primary-alkyl esters of carboxylic acids. Methyl carboxylate, ethyl carboxylate, and n-propyl carboxylate are preferred on account of their prices and easy progress of the reaction. An amount of the alkyl carboxylate is 0.8 to 500 moles, preferably 0.8 to 50 moles, further preferably 0.8 to 5 moles, per mole of the starting material, compound (3).

Example of the catalyst to be used in the transesterification include inorganic acids such as hydrochloric acid, hydrobromic acid, sulfuric acid and nitric acid; organic acids such as oxalic acid, trifluoroacetic acid, methanesulfonic acid, benzenesulfonic acid and p-toluenesulfonic acid; bases such as sodium methoxide, sodium ethoxide, potassium t-butoxide and 4-dimethylaminopyridine; salts such as sodium cyanide, potassium cyanide, sodium acetate, potassium acetate, calcium acetate, tin acetate, aluminum acetate, aluminum acetoacetate and alumina; and Lewis acids such as aluminum trichloride, aluminum ethoxide, aluminum isoporopoxide, aluminum oxide, boron trifluoride, boron trichloride, boron tribromide, magnesium chloride, magnesium bromide, magnesium iodide, zinc chloride, zinc bromide, zinc iodide, tin tetrachloride, tin tetrabromide, dibutyltin dichloride, dibutyltin dimethoxide, dibutyltin oxide, titanium tetrachloride, titanium tetrabromide, titanium(IV) methoxide, titanium(IV) ethoxide, titanium(IV) isopropoxide and titanium(IV) oxide. These may be used alone or in combination. An amount of the catalyst is 0.0001 to 100 moles, preferably 0.001 to 1 mole, more preferably 0.01 to 0.05 mole, per mole of the starting material, compound (3).

Transesterification may be carried out without a solvent or in a condition where the reactant, alkyl carboxylate, itself is a solvent. This embodiment is preferred, because additional operations such as condensation or recovery of a solvent are unnecessary. It is possible to use a solvent as an auxiliary means. In such a case, examples of the solvent include hydrocarbons such as hexane, heptane, benzene, toluene, xylene and cumene; ethers such as diethyl ether, di-n-butyl ether, diethyleneglycol diethyl ether, diethyleneglycol dimethyl ether, tetrahydrofurane and 1,4-dioxan. These may be used alone or in combination. A proper reaction temperature may be chosen, depending upon an alkyl carboxylate to be used and reaction conditions. Usually, the reaction is carried out with heating at a temperature near a boiling point of a lower alcohol which occurs in the transesterification and has a low boiling temperature, such as methanol, ethanol or 1-propanol, and the resultant lower alcohol is continuously distilled off. This embodiment gives a better result. The alcohol may be distilled off, in a reduced pressure, at a temperature lower than its boiling point.

In the embodiment where compound (3), (2,3,4,4-tetramethylcyclopentyl)methanol, is converted into an alkylating agent, which is then reacted with a carboxylic acid, compound (3) is first converted, for instance, into a corresponding halide, such as chloride, bromide or iodide, or into a corresponding sulfonate, such as methane sulfonate, trifluoromethane sulfonate, benzene sulfonate or p-toluene sulfonate, which is then reacted with a carboxylic acid, usually in a solvent and in a basic condition. Alternatively, (2,3,4,4-tetramethylcyclopentyl)methanol (3) is mixed with triphenylenephosphine and diethyl azodicarboxylate and then reacted with a carboxylic acid, usually in a solvent. A solvent, a base, a reaction time and a reaction temperature may be as mentioned for the reaction of compound (3) with an acylating agent. In place of the combination of a carboxylic acid with a base, use may be made of sodium carboxylate, lithium carboxylate, potassium carboxylate or ammonium carboxylate.

When a starting material in the transesterification is (2,3,4,4-tetramethylcyclopentyl)methanol (3') represented by the following formula (3'), then (2,3,4,4-tetramethylcyclopentyl) methyl carboxylate compound represented by the following formula (4') is obtained, which has the same relative stereo-configuration as that of (2,3,4,4-tetramethylcyclopentyl)methyl acetate, sex pheromone of OMB.

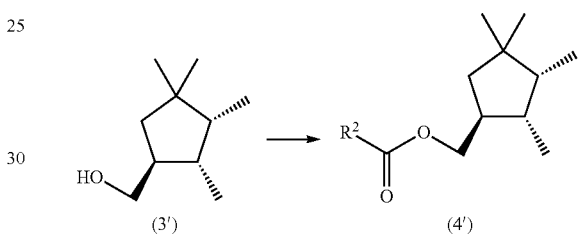

Isolation and purification of (2,3,4,4-tetramethylcyclopentyl) methyl carboxylate compound (4) thus obtained may be carried out in any conventional manner properly chosen from ones usually used in organic syntheses, such as reduced-pressure distillation and various chromatographyies. Reduced-pressure distillation is preferred in view of industrial economy.

As stated above, the methods for the preparations of the 2,3,4,4-tetramethylcyclopentane compound (2), (2,3,4,4-tetramethylcyclopentyl)methanol (3) and the (2,3,4,4-tetramethylcyclopentyl)methyl carboxylate compound (4) are now provided, which methods are of a short process and efficient to provide those envisaged materials in amounts sufficient for practical applications.

EXAMPLES

The present invention will be explained in detail with reference to the following non-limitative Examples.

The purities of starting materials, products and intermediates are determined by gas chromatography (GC), and expressed as "% GC". Gas chromatography conditions are as follows:

GC apparatus, Simazdu GC-14A; column, 5% Ph-Me silicone, 0.25 mmφX25 m; carrier gas, He; and detector, FID.

Purities of starting materials and the resulting products are not necessarily 100%. Accordingly, a yield hereinafter will be a reduced yield calculated in accordance with the following equation, based on % GC. Compounds have various sensitivities in GC. Accordingly, reduced yields might exceed 100%, particularly for impure starting materials and impure products.

In order to prepare a sample for spectrum analysis, crude products are purified, if necessary.

Reduced yield in %=(weight of a product obtained in a reaction multiplied by its % GC)/molecular weight of a product)*100/(weight of a starting material used in a reaction multiplied by its % GC)/molecular weight of a starting material)

Hereinafter, reduced yield will simply be called "yield".

Reference Example 1

Synthesis:
3,5,5-trimethyl-4-methylidene-2-cyclohexene-1-one
(5)

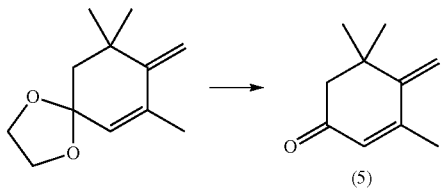

To a mixture of 75.4 g of 1,4-dioxaspiro[4.5]-8-methylidene-7,9,9-trimethyl-6-decene (91.8% GC) and 335 g of diethyl ether in a nitrogen atmosphere, added was 67 g of 20% hydrochloric acid at room temperature with stirring. After stirring at room temperature for two hours, 335 g of water was added, and an organic layer and an aqueous layer were separated. The separated organic layer was subjected to usual after-treatment, i.e., washing, drying and condensation, to obtain 58.7 g of the envisaged 3,5,5-trimethyl-4-methylidene-2-cyclohexene-1-one as a yellowish oil (91.5% GC, yield: 100%).

The analytical results of this material are as follow.

IR(D-ATR): ν=2966, 2875, 1712, 1668, 1587, 1443, 1407, 1381, 1366, 1284, 1251, 1112, 913 cm$^{-1}$ $^1$H-NMR (500 MHz, CDCl$_3$): δ=1.18 (6H, s), 2.06 (3H, d, J=1.2 Hz), 2.33 (2H, s), 5.36 (1H, d, J=2.0), 5.43 (1H, s), 5.90 (1H, s) ppm $^{13}$C-NMR (125 MHz, CDCl$_3$): δ=20.86, 28.54, 38.23, 51.82, 114.25, 126.88, 151.57, 153.38, 199.26 ppm GC-MS(EI, 70 eV): 27, 39, 51, 66, 79, 91, 107, 122, 135, 150 (M$^+$)

Example 1

Synthesis of 3,3,4,5-tetramethylcyclohexane-1-one Represented by the Following Formula (6') as an Example of 3,3,4,5-tetramethylcyclohexane-1-one (6)

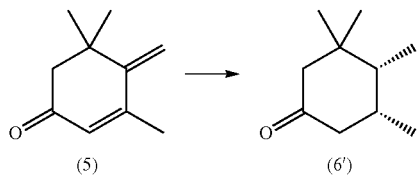

To a mixture of 21.4 g of 3,5,5-trimethyl-4-methylidene-2-cyclohexene-1-one (84.3% GC) and 200 g of ethanol in a nitrogen atmosphere, added was 1.7 g of palladium carbon at room temperature with stirring. After stirring for two hours at room temperature in a hydrogen atmosphere, the reaction mixture was subjected to usual after-treatment, i.e., filtration and condensation, to obtain 20.4 g of the envisaged 3,3,4,5-tetramethylcyclohexane-1-one as a yellowish oil (75.0% GC, yield: 83%). According to GC-MS analysis, a ratio of syn-isomer/anti-isomer was 94:6.

IR(D-ATR): ν=2962, 2873, 1716, 1456, 1419, 1383, 1370, 1347, 1309, 1277, 1252, 1230, 1183, 1169, 1138, 1047, 1010, 893, 845, 617 cm$^{-1}$ $^1$H-NMR (500 MHz, CDCl$_3$): δ=0.95 (9H, m), 0.98 (3H, s), 1.44 (1H, dq, J=7.3, 3.9 Hz), 1.89 (1H, dt, J=14.2, 1.5 Hz), 2.05 (1H, d, J=13.8 Hz), 2.09 (1H, dd, J=14.2, 2.0 Hz), 2.28 (1H, d, J=13.8 Hz), 2.32 (1H, m) ppm $^{13}$C-NMR (125 MHz, CDCl$_3$): δ=7.70, 19.67, 28.34, 28.81, 31.71, 38.01, 42.70, 44.06, 49.45, 212.05 ppm GC-MS(EI, 70 eV): 27, 41, 56, 69, 83, 98, 111, 125, 139, 154 (M$^+$)

Example 2

Synthesis of Alpha-Bromotetramethylcyclohexanone Represented by the Following Formula (1a') or (1b') as an Example of Alpha-Halotetramethylcyclohexanone (1a) or (1b)

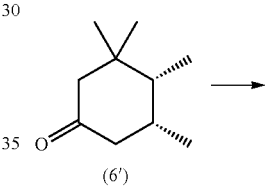

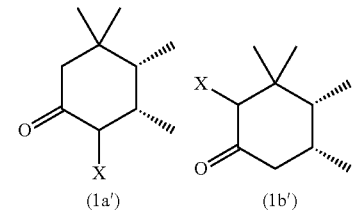

wherein X represents a bromine atom.

To a mixture of 10.2 g of 3,3,4,5-tetramethylcyclohexane-1-one (91.0% GC) and 60 g of diethyl ether in a nitrogen atmosphere, added was 10.1 g of bromine at 0 degree C. with stirring. After stirring at 0 degree C. for one hour, 110 g of a mixture of an aqueous solution of sodium hydrogen carbonate and an aqueous solution of sodium thiosulfate was added, and an organic layer and an aqueous layer were separated. The separated organic layer was subjected to usual after-treatment, i.e., washing, drying and condensation, to obtain 14.6 g of the envisaged alpha-bromotetramethylcyclohexanone as a yellowish oil (89.7% GC, yield: 93%), which was a diastereomer mixture.

IR(D-ATR): ν=2960, 2875, 1728, 1456, 1424, 1385, 1371, 1347, 1274, 1177, 1142, 1125, 1069, 1063, 1047, 989, 343, 887, 858, 808, 775, 132, 629, 570 cm$^{-1}$ $^1$H-NMR (500 MHz, CDCl$_3$): δ=0.94~1.25 (12H, m), 1.76 (1H, m), 2.20~2.53 (3H, m), 4.28 (0.7H, d, J=11.5 Hz), 4.72 (0.3H, s) ppm GC-MS(EI, 70 eV): 41, 55, 69, 83, 97, 232 (M$^+$)

Example 3

Synthesis No. 1 of Methyl 2,3,4,4-Tetramethylcyclopentane Carboxylate Represented by the Following Formula (2') as an Example of the 2,3,4,4-Tetramethylcyclopentane Compound (2)

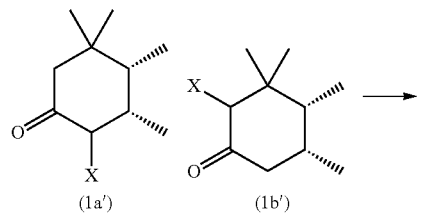

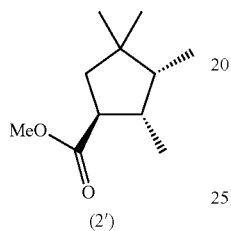

wherein $R_1$=$CH_3$ or Me.

To a mixture of 2.60 g of alpha-bromotetramethylcyclohexanone (80.4% GC) and 10 g of methanol in a nitrogen atmosphere, added was 2.60 g of a 28% solution of sodium methoxide in methanol at room temperature with stirring. After stirring at room temperature for two hours, the reaction mixture was heated with stirring under reflux for two hours and cooled to room temperature. 24 Gram of diluted hydrochloric acid was added, and an organic layer and an aqueous layer were separated. The separated organic layer was subjected to usual after-treatment, i.e., washing, drying and condensation, to obtain 1.81 g of the envisaged methyl 2,3,4,4-tetramethylcyclopentane carboxylate as a yellowish oil (33.2% GC, yield: 36%).

$^1$H-NMR (500 MHz, CDCl$_3$): δ=0.76 (3H, d, J=7.6 Hz), 0.84 (3H, s), 0.97 (3H, d, J=6.9 Hz), 1.00 (3H, s) 1.62-1.77 (3H, m), 2.41-2.50 (2H, m), 3.64 (3H, s) ppm $^{13}$C-NMR (125 MHz, CDCl$_3$): δ=10.17, 16.99, 23.73, 29.43, 40.22, 41.82, 43.94, 46.17, 50.02, 51.52, 177.33 ppm GC-MS(EI, 70 eV): 29, 41, 55, 69, 87, 98, 109, 128, 137, 153, 169, 184 (M$^+$)

Example 4

Synthesis No. 2 of Methyl 2,3,4,4-tetramethylcyclopentane Carboxylate Represented by the Following Formula (2') as an Example of the 2,3,4,4-tetramethylcyclopentane Compound (2)

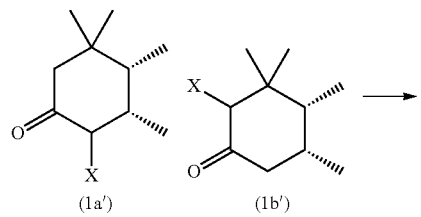

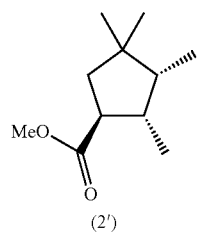

wherein $R^1$=$CH_3$ or Me.

Tetrahydrofurane was used instead of methanol used in Example 3 to carry out similar reactions as in Example 3. The envisaged methyl 2,3,4,4-tetramethylcyclopentane carboxylate was obtained in a yield of 30%.

Example 5

Synthesis No. 3 of Methyl 2,3,4,4-tetramethylcyclopentane Carboxylate Represented by the Following Formula (2') as an Example of the 2,3,4,4-tetramethylcyclopentane Compound (2)

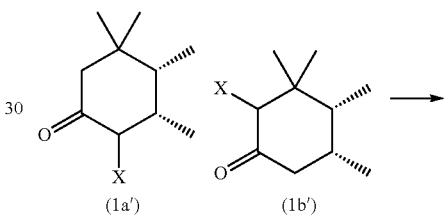

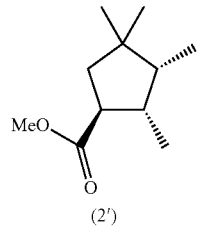

wherein $R^1$=$CH_3$ or Me.

Toluene was used instead of methanol used in Example 3 to carry out similar reactions as in Example 3. The envisaged methyl 2,3,4,4-tetramethylcyclopentane carboxylate was obtained in a yield of 28%.

Example 6

Synthesis No. 1 of 2,3,4,4-tetramethylcyclopentanoic Acid Represented by the Following Formula (2') as an Example of the 2,3,4,4-tetramethylcyclopentane Compound (2)

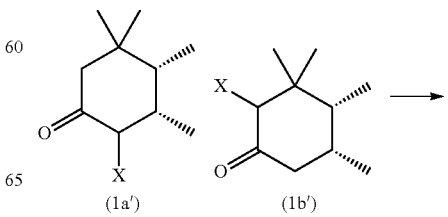

-continued

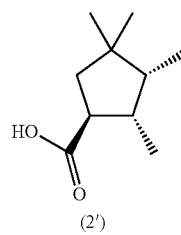

(2')

wherein R¹=H.

To a mixture of 2.45 g of alpha-bromotetramethylcyclohexanone (85.0% GC), 5 g of methanol and 5 g of water in a nitrogen atmosphere, added was 2 g of an aqueous 25% solution of sodium hydroxide at room temperature with stirring. After stirring at room temperature for two hours, the reaction mixture was heated with stirring under reflux for 10 hours and cooled to room temperature. 20 Gram of diluted hydrochloric acid was added, and an organic layer and an aqueous layer were separated. The separated organic layer was subjected to usual after-treatment, i.e., washing, drying and condensation, to obtain 1.07 g of the envisaged methyl 2,3,4,4-tetramethylcyclopentanoic acid as a yellowish oil (48.3% GC, yield: 34%).

¹H-NMR (500 MHz, CDCl₃): δ=0.76 (3H, d, J=7.6 Hz), 0.86 (3H, s), 1.02 (3H, s), 1.02 (3H, d, J=5.4 Hz), 1.66-1.76 (3H, m), 2.45-2.55 (2H, m), 10.90 (1H, brs) ppm ¹³C-NMR (125 MHz, CDCl₃): δ=10.18, 16.98, 23.74, 29.43, 40.33, 41.92, 43.67, 46.32, 49.99, 183.50 ppm GC-MS(EI, 70 eV): 29, 41, 55, 69, 82, 97, 109, 123, 141, 154 (M⁺)

Example 7

Synthesis No. 2 of 2,3,4,4-tetramethylcyclopentanoic Acid Represented by the Following Formula (2') as an Example of the 2,3,4,4-tetramethylcyclopentane Compound (2)

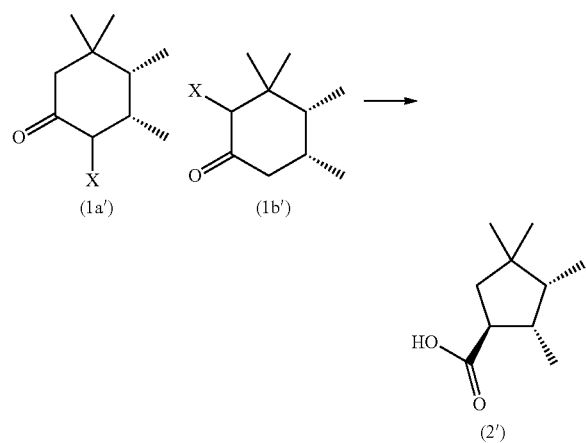

wherein R¹=H.

t-Butyl alcohol was used instead of water and methanol used in Example 6 and potassium t-butoxide was used instead of sodium hydroxide to carry out similar reactions as in Example 6. The envisaged 2,3,4,4-tetramethylcyclopentanoic acid was obtained in a yield of 35%.

Example 8

Synthesis No. 3 of 2,3,4,4-tetramethylcyclopentanoic Acid Represented by the Following Formula (2') as an Example of the 2,3,4,4-tetramethylcyclopentane Compound (2)

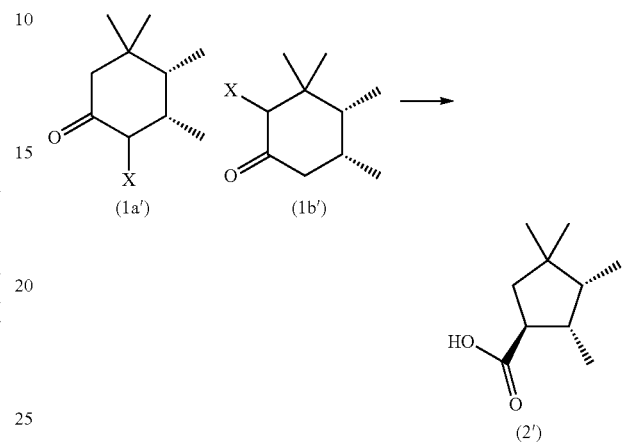

wherein R¹=H.

THF was used instead of methanol used in Example 6 to carry out similar reactions as in Example 6. The envisaged 2,3,4,4-tetramethylcyclopentanoic acid was obtained in a yield of 22%.

Example 9

Synthesis of (2,3,4,4-tetramethylcyclopentyl)methanol Represented by the Following Formula (3') as an Example of the (2,3,4,4-tetramethylcyclopentyl)methanol (3)

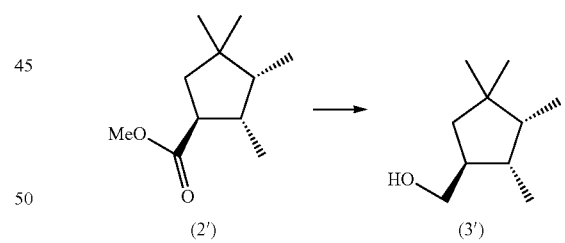

To a mixture of 0.89 g of lithium aluminum hydride and 5 g of tetrahydrofurane in a nitrogen atmosphere, dropwise added were 3.06 g of methyl 2,3,4,4-tetramethylcyclopentane carboxylate (35.3% GC) and 20 g of tetrahydrofurane at 0 degree C. with stirring. After stirring at room temperature overnight, g of an aqueous solution of sodium hydroxide was added and the reaction mixture was filtered. The resultant filtrate was subjected to usual after-treatment, i.e., washing, drying and condensation, to obtain 2.65 g of the envisaged (2,3,4,4-tetramethylcyclopentyl)methanol as a yellowish oil (31.6% GC, yield: 92%).

¹H-NMR (500 MHz, CDCl₃): δ=0.78 (3H, d, J=7.3 Hz), 0.85 (3H, s), 0.95 (3H, d, J=6.9 Hz), 0.96 (3H, s), 1.15 (1H, dd, J=12.2, 9.2 Hz), 1.60-1.70 (2H, m), 1.77-1.92 (2H, m), 3.52 (1H, m), 3.65 (1H, m) ppm $^{13}$C-NMR (125 MHz, CDCl$_3$): δ=10.21, 17.40, 23.82, 29.73, 38.57, 41.31, 44.45, 46.15, 48.17, 67.47 ppm GC-MS(EI, 70 eV): 29, 41, 55, 69, 82, 97, 109, 123, 141, 154 (M$^+$)

Example 10

Synthesis of (2,3,4,4-tetramethylcyclopentyl)methanol Represented by the Following Formula (3') as an Example of the (2,3,4,4-tetramethylcyclopentyl) methanol (3)

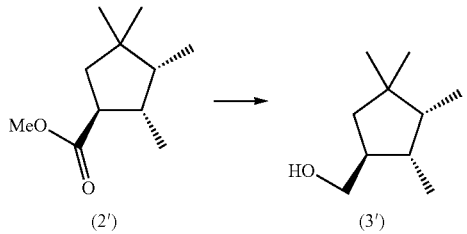

To a mixture of 0.57 g of lithium aluminum hydride and 5 g of tetrahydrofurane in a nitrogen atmosphere, dropwise added were 1.78 g of 2,3,4,4-tetramethylcyclopentanoic acid (43.3% GC) and 20 g of tetrahydrofurane at 0 degree C. with stirring. After stirring at room temperature overnight, 45 g of an aqueous solution of sodium hydroxide was added and the reaction mixture was filtered. The resultant filtrate was subjected to usual after-treatment, i.e., washing, drying and condensation, to obtain 1.78 g of the envisaged (2,3,4,4-tetramethylcyclopentyl)methanol (45.3% GC, yield: 114%).

Example 11

Synthesis of (2,3,4,4-tetramethylcyclopentyl) methyl Acetate Represented by the Following Formula (4') as an Example of (2,3,4,4-tetramethylcyclopentyl) methyl Carboxylate (4)

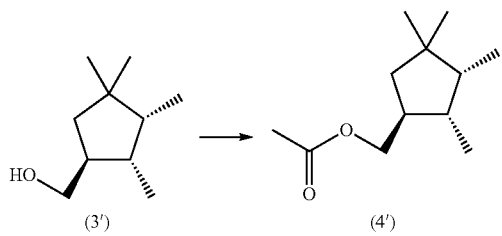

wherein R$^2$=CH$_3$ or Me.

To a mixture of 1.78 g of (2,3,4,4-tetramethylcyclopentyl) methanol (45.3% GC), 1.04 g of pyridine and 20 g of acetonitrile in a nitrogen atmosphere, dropwise added was 0.95 g of acetyl chloride at 0 degree C. with stirring. After stirring at room temperature for two hours, 40 g of water was added, and an organic layer and an aqueous layer were separated. The separated organic layer was subjected to usual after-treatment, i.e., washing, drying and condensation, to obtain 2.11 g of the envisaged (2,3,4,4-tetramethylcyclopentyl) methyl acetate as a yellowish oil (45.5% GC, yield: 94%).

$^1$H-NMR (500 MHz, CDCl$_3$): δ=0.77 (3H, d, J=7.3 Hz), 0.84 (3H, s), 0.93 (3H, d, J=6.9 Hz), 0.95 (3H, s), 1.13 (1H, dd, J=12.6, 9.2 Hz), 1.60-1.67 (2H, m), 1.86-1.95 (2H, m), 2.03 (3H, s), 3.97 (1H, m), 4.04 (1H, m) ppm $^{13}$C-NMR (125 MHz, CDCl$_3$): δ=10.17, 17.09, 20.97, 23.78, 39.05, 41.22, 44.42, 44.46, 46.14, 68.70, 171.30 ppm GC-MS(EI, 70 eV): 29, 43, 55, 69, 82, 97, 109, 123, 138, 155, 165, 183 (M$^+$)

The invention claimed is:

1. A method for the preparation of a (2,3,4,4-tetramethylcyclopentyl)methyl carboxylate compound, comprising
a step of subjecting alpha-halotetramethylcyclohexanone corresponding to the following general formula (1a) or (1b):

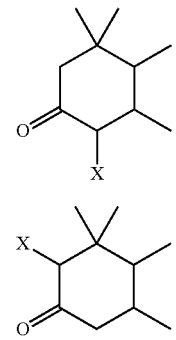

(1a)

(1b)

wherein X is a chlorine atom or a bromine atom,
to a Favorskii rearrangement to obtain a 2,3,4,4-tetramethylcyclopentane compound corresponding to the following general formula (2):

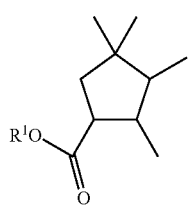

(2)

wherein R$^1$ is a hydrogen atom or a monovalent C$_{1-15}$ hydrocarbon group,
a step of subjecting 2,3,4,4-tetramethylcyclopentane compound (2) to reduction to obtain (2,3,4,4-tetramethylcyclopentyl)methanol corresponding to the following general formula (3):

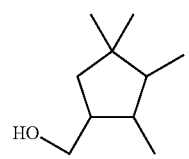

(3)

and a step of subjecting (2,3,4,4-tetramethylcyclopentyl)methanol (3) to acylation to obtain a (2,3,4,4-tetramethylcyclopentyl)methyl carboxylate compound corresponding to the following general formula (4):

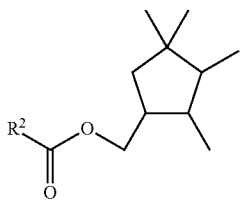 (4)

wherein R² is a monovalent $C_{1-15}$ hydrocarbon group.

2. Alpha-halotetramethylcyclohexanone corresponding to the following general formula (1a) or (1b):

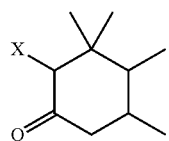 (1a)

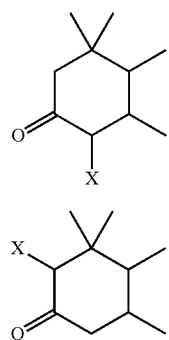 (1b)

wherein X is a chlorine atom or a bromine atom.

3. A method for the preparation of alpha-halotetramethylcyclohexanone, comprising
a step of hydrogenating 3,5,5-trimetyl-4-methylidene-2-cyclohexene-1-one corresponding to the following formula (5):

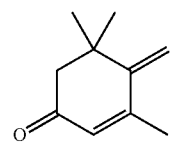 (5)

to obtain 3,3,4,5-tetramethylcyclohexane-1-one corresponding to the following formula (6):

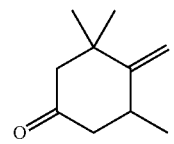 (6)

and a step of subjecting 3,3,4,5-tetramethylcyclohexane-1-one (6) to halogenation to obtain alpha-halotetramethylcyclohexanone corresponding to said general formula (1a) or (1b).

* * * * *